United States Patent
Choi et al.

(10) Patent No.: US 12,396,842 B2
(45) Date of Patent: *Aug. 26, 2025

(54) OPHTHALMIC LENSES HAVING AN EXTENDED DEPTH OF FOCUS FOR IMPROVING INTERMEDIATE VISION

(71) Applicant: Alcon Inc., Fribourg (CH)

(72) Inventors: Myoung-Taek Choi, Arlington, TX (US); Sangyeol Lee, North Richland Hills, TX (US); Shinwook Lee, Arlington, TX (US); Wangkuen Lee, Arlington, TX (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/407,726

(22) Filed: Jan. 9, 2024

(65) Prior Publication Data
US 2024/0148490 A1    May 9, 2024

Related U.S. Application Data

(63) Continuation of application No. 17/231,374, filed on Apr. 15, 2021, now Pat. No. 11,903,819.

(60) Provisional application No. 63/010,792, filed on Apr. 16, 2020.

(51) Int. Cl.
  *A61F 2/16* (2006.01)

(52) U.S. Cl.
  CPC .......... *A61F 2/1627* (2013.01); *A61F 2/1616* (2013.01); *A61F 2/1632* (2013.01); *A61F 2/164* (2015.04)

(58) Field of Classification Search
  CPC ...................................................... A61F 2/164
  See application file for complete search history.

(56) References Cited

U.S. PATENT DOCUMENTS

| | | | |
|---|---|---|---|
| 7,061,693 B2 | 6/2006 | Zalevsky | |
| 8,057,541 B2 | 11/2011 | Dishler | |
| RE45,969 E | 4/2016 | Hong | |
| 9,968,440 B2 | 5/2018 | Hong et al. | |
| 10,871,659 B2 | 12/2020 | Hong | |
| 2005/0036105 A1* | 2/2005 | Perel | G02C 7/044 |
| | | | 351/159.41 |
| 2010/0016965 A1 | 1/2010 | Hong | |
| 2016/0058553 A1 | 3/2016 | Salahieh | |
| 2017/0219846 A1* | 8/2017 | Ando | A61F 2/1654 |

(Continued)

FOREIGN PATENT DOCUMENTS

WO        2014091528 A1    6/2014

*Primary Examiner* — Javier G Blanco
(74) *Attorney, Agent, or Firm* — PATTERSON + SHERIDAN, LLP

(57) ABSTRACT

The present disclosure provides an ophthalmic lens (such as an IOL) that is designed to enhance depth of focus for intermediate vision performance, while maintaining distance vision. The lens may include an optic having an anterior surface and a posterior surface disposed about an optical axis. One of the surfaces (e.g., the anterior surface) may have a surface profile involving a superposition of at least three structures or profiles, including a base structure, a phase shift structure having an inner region, an outer region and a transition region, and a zonal structure having an inner power zone and an outer transition zone.

20 Claims, 7 Drawing Sheets

(56) References Cited

U.S. PATENT DOCUMENTS

| | | | | |
|---|---|---|---|---|
| 2018/0132996 A1* | 5/2018 | Tiwari | ................. | A61F 2/1654 |
| 2022/0401210 A1* | 12/2022 | Sanger | ................. | A61F 2/1618 |

\* cited by examiner

OPHTHALMIC LENSES HAVING AN EXTENDED DEPTH OF FOCUS FOR IMPROVING INTERMEDIATE VISION

PRIORITY CLAIM

This application is a continuation of U.S. patent application Ser. No. 17/231,374, filed on Apr. 15, 2021, which claims the benefit of priority of U.S. Provisional Patent Application Ser. No. 63/010,792 titled "OPHTHALMIC LENSES HAVING AN EXTENDED DEPTH OF FOCUS FOR IMPROVING INTERMEDIATE VISION," filed on Apr. 16, 2020, whose inventors are Myoung-Taek Choi, Sangyeol Lee, Shinwook Lee and Wangkuen Lee, which are hereby incorporated by reference in their entirety as though fully and completely set forth herein.

FIELD

The present disclosure generally relates to the field of ophthalmic lenses, and more specifically to lenses having an extended depth of focus for improving intermediate vision.

BACKGROUND

Ophthalmic lenses, such as intraocular lenses, are routinely implanted in patients' eyes during cataract surgery to replace the natural crystalline lenses. The optical power of the natural crystalline lens can vary under the influence of the ciliary muscles to provide accommodation for viewing objects at different distances from the eye. Many intraocular lenses provide improved distance performance, but may lack provision for extended depth of focus for intermediate vision.

SUMMARY

The present disclosure is generally directed to an ophthalmic lens (such as an IOL) that enhances depth of focus for intermediate vision performance, while maintaining distance vision.

In accordance with the present disclosure, the lens includes an optic having an anterior surface and a posterior surface disposed about an optical axis, at least one of the anterior and posterior surfaces having a surface profile corresponding to a superposition of at least three profiles. The three profiles include a phase shift structure, a zonal structure, and a base structure or curvature. The phase shift structure is characterized by an inner region, an outer region, and a transition region. The inner region extends radially from the optical axis to a first boundary. The transition region is disposed between the inner region and the outer region and extends radially from the first boundary to a second boundary, wherein the transition region is adapted such that a phase of radiation incident thereon varies linearly over at least a portion of the radial extent between the first boundary and the second boundary so as to generate a phase shift between the first and second boundaries. The second boundary is disposed at a radial distance further from the optical axis than the first boundary. The outer region extends radially from the second boundary towards an outermost edge of the optic. The zonal structure includes an inner power zone having a first curvature and an outer transition zone having a second curvature. The inner power zone extends radially from the optical axis to the second boundary, and the outer transition zone extends radially to a third boundary. The third boundary is disposed at a radial distance further from the optical axis than the second boundary. The base curvature extends radially from the third boundary to the outermost edge of the optic.

As understood by one of ordinary skill in the art, the drawings described below are for illustration purposes only, and are not intended to limit the scope of the present disclosure.

DETAILED DESCRIPTION

Intraocular lenses (IOLs) are the most common type of lenses used with cataract surgery. Monofocal IOLs are intraocular lenses having a single point of focus for one distance, e.g., near-distance focus, mid-distance focus, or long-distance focus. Since a monofocal IOL may only be set for one distance, and because most patients and practitioners opt for long-distance focus, patients may be required to utilize additional eyewear to correct for vision at near and/or intermediate visions. Additionally, as human eyes age, depth of focus diminishes. Depth of focus (measured in diopters, D) is the total distance in front of and behind the focal point over which the image may be focused without causing a sharpness reduction beyond a certain tolerable amount. Conventional monofocal IOLs are limited in extending depth of focus.

The present disclosure is generally directed to an ophthalmic lens (such as a monofocal IOL) having a surface profile that maintains distance image quality while improving intermediate vision, and further extends depth of focus. Although the following disclosure is described in conjunction with IOLs, it is to be understood that the features and elements of the present disclosure are not to be limited to any particular type of IOL and may be applied to monofocal or multifocal IOLs. Additionally, the present disclosure may further be applied to non-IOL ophthalmic lenses, such as contact lenses. Moreover, as used herein, the term "intraocular lenses" (and its abbreviation IOL) is used to describe lenses that are implanted into the interior of the eye to either replace the eye's natural lens or to otherwise augment vision regardless of whether the natural lens is removed.

Figure 1A:
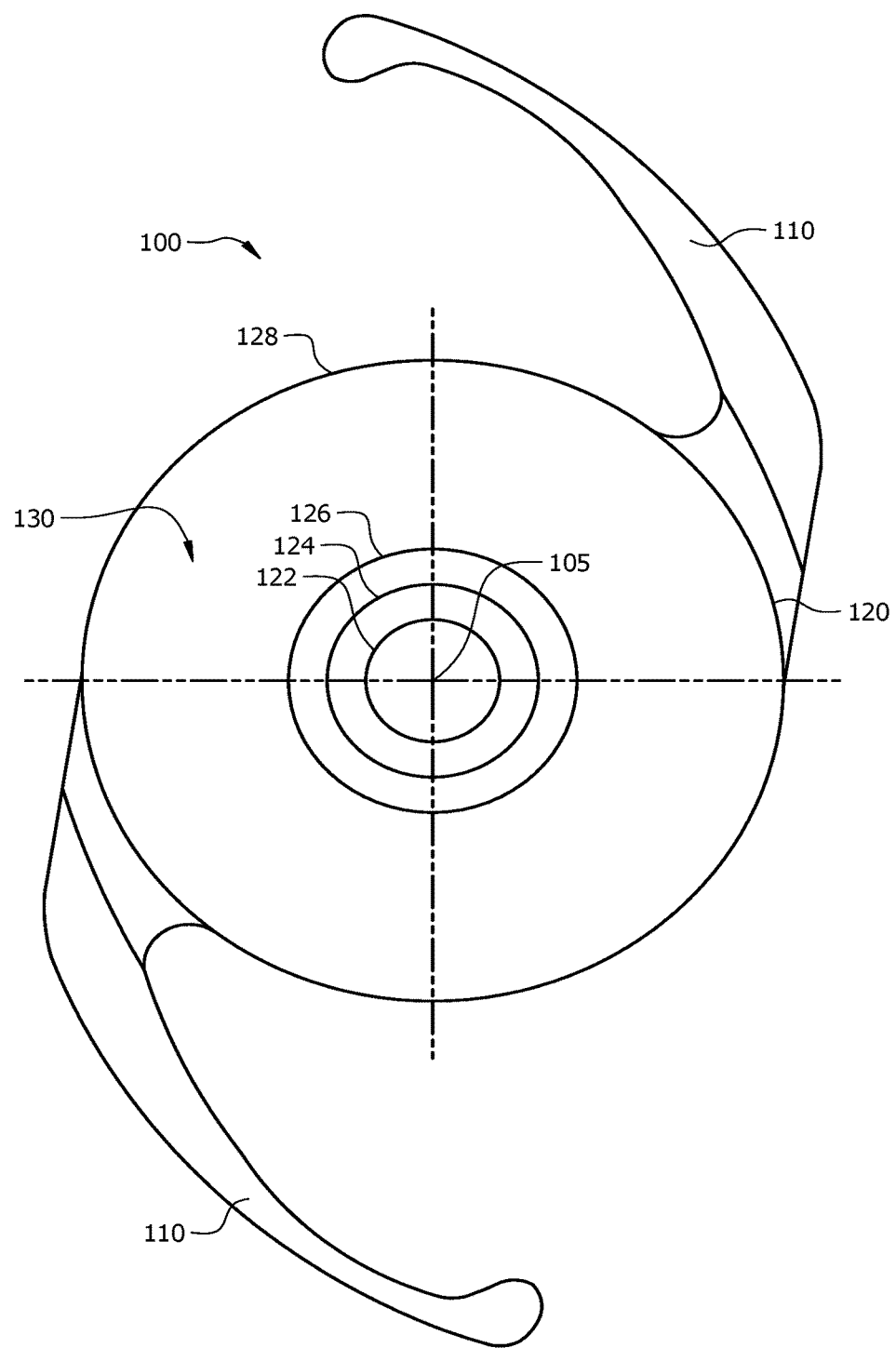
FIG. 1A illustrates a top view of an example embodiment of an ophthalmic lens, in accordance with the present disclosure.
Figure 1B:
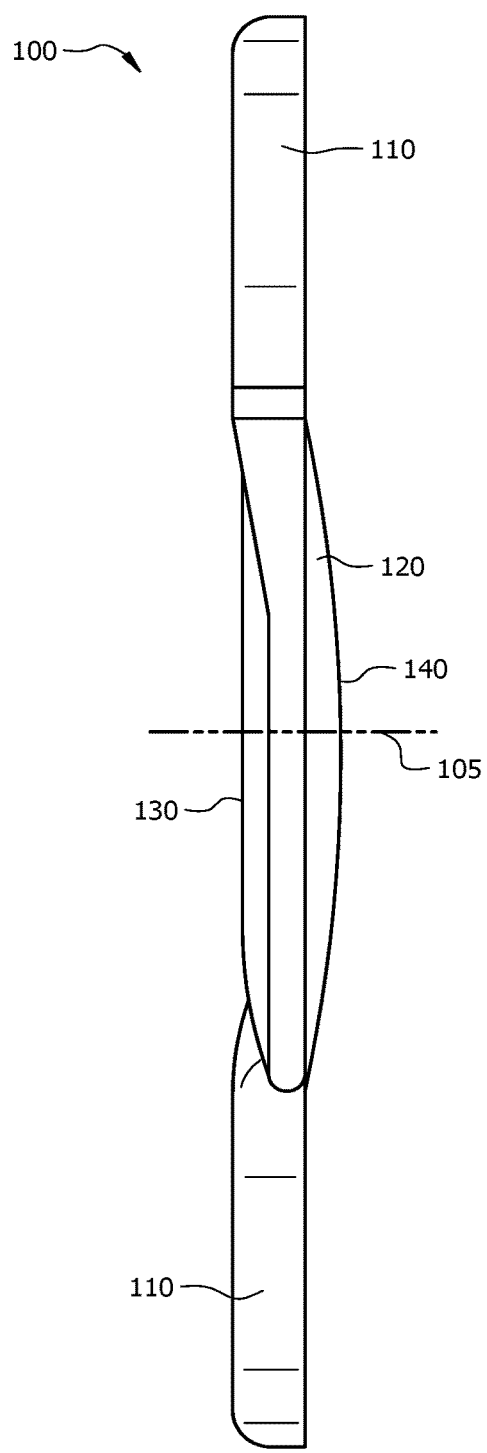
FIG. 1B illustrates a side view of an example embodiment of an ophthalmic lens, in accordance with the present disclosure.

Reference is now made to FIGS. 1A and 1B, wherein are depicted an example embodiment of an intraocular lens 100 according to the present disclosure. FIG. 1A depicts a top view of an anterior surface 130 of the lens 100, and FIG. 1B depicts a side view showing the anterior 130 and the posterior 140 surfaces of the lens 100. Lens 100 may comprise a plurality of haptics 110 generally operable to position and stabilize the lens 100 within the capsular bag of a patient's eye. Lens 100 may further comprise an optic 120 having an anterior surface 130 and a posterior surface 140 that are disposed about an optical axis 105 of the lens. As shown in FIGS. 1A and 1B, optical axis 105 passes through the geometrical center of the optic 120. One of the anterior 130 and posterior 140 surfaces may comprise either an aspheric or a spherical surface profile, and the other of the surfaces may comprise a multi-layered surface profile formed by the superposition of three profiles or structures. For purposes of illustration, the multi-layered surface profile is depicted on the anterior surface 130 of the optic 120 in FIG. 1A. However, it is to be understood that the multi-layered surface profile shown and described in conjunction with FIG. 1A may alternatively be applied on the posterior surface 140 of the optic 120, and an aspheric or spherical surface profile may be applied on the anterior surface 130 of the optic 120.

Figure 2:
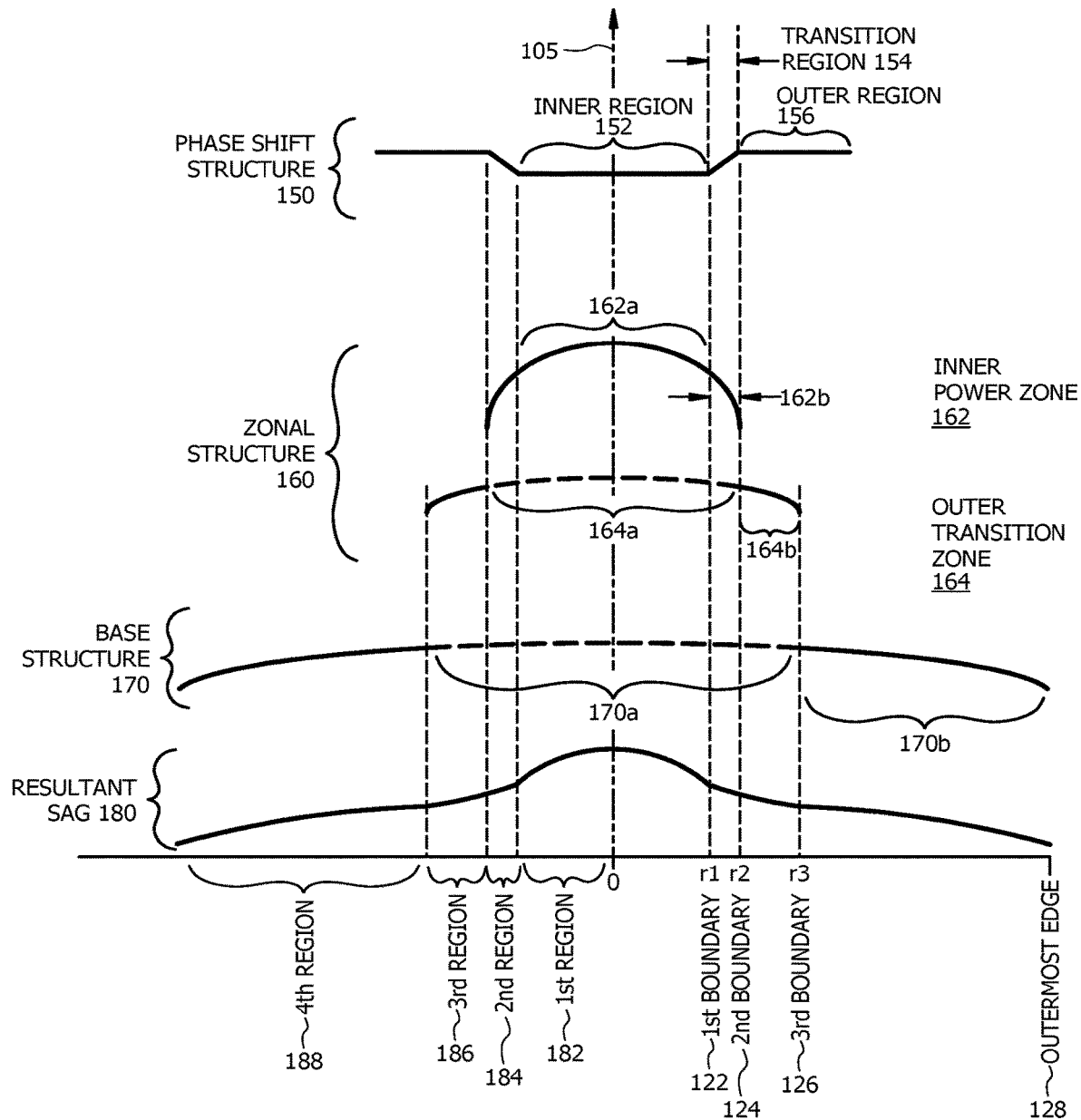
FIG. 2 illustrates an exploded cross-sectional view of the layers and the resultant sag of an example optic, in accordance with the present disclosure.

Reference is now made to FIG. 1A in conjunction with FIG. 2. FIG. 2 illustrates an exploded cross-sectional view showing the individual layers or structures 150, 160, 170 which form the multi-layered surface profile of the anterior surface 130 of the optic 120, as well as the composite or resultant sag 180 of the anterior surface 130 of the optic 120. FIG. 1A illustrates an overhead (top) view of the composite multi-layered surface profile of the anterior surface 130 of the optic 120, with radial boundaries 122, 124, 126, 128 in FIG. 1A corresponding to the boundaries of structures 150, 160, 170 in FIG. 2. In FIG. 2, it is to be understood that the left and right sides of the optical axis 105 mirror each other. Therefore, the structures, boundaries, and designations shown on a given side of the optical axis 105 may apply equally to the other side of the optical axis 105.

The multi-layered surface profile of the anterior surface 130 may include the superposition of at least three profiles or structures: a phase shift structure 150; an aspheric zonal structure 160; and an aspheric base structure 170. The zonal structure 160 may further include the superposition of an inner power zone 162 and an outer transition zone 164. As discussed above, each of these structures may be defined in conjunction with a plurality of radial boundaries 122, 124, 126, 128 formed at increasing radial distances from the optical axis 105 of the optic 120. The multi-layered surface profile ($Z_{total}$) of the anterior surface 130 of the optic 120—comprising the phase shift structure 150, the zonal structure 160, and the base structure 170—may be defined by the following equation:

$$Z_{total} = Z_{max} + Z_{zone1} + Z_{zone2} + Z_{base} \quad \text{Eq. (1)},$$

wherein, $Z_{max}$ represents the surface profile of the phase shift structure 150;

$Z_{zone1}$ represents the surface profile of the inner power zone 162 of the zonal structure 160;

$Z_{zone2}$ represents the surface profile of the outer transition zone 164 of the zonal structure 160; and $Z_{base}$ represents the surface profile of the base structure 170.

Each of these structures 150, 160, 170 will be described in turn.

First, the phase shift structure 150 may comprise a trapezoid phase shift (TPS) feature having an inner region 152, a transition region 154; and an outer region 156. The inner region 152 may extend radially from the optical axis 150 to a first radial boundary 122. The transition region 154 may extend radially from the first radial boundary 122 to a second radial boundary 124, which is disposed at a radial distance further from the optical axis 105 than the first radial boundary 122. The transition region 154 may be configured such that a phase of radiation incident thereon varies linearly over at least a portion of the radial extent between the first radial boundary 122 and the second radial boundary 124 so as to generate a phase shift between the first radial boundary 122 and the second radial boundary 124. The outer region 156 of the phase shift structure 150 may extend radially from the second radial boundary 124 to an outermost edge 128 of the optic 120.

The trapezoid phase shift structure 150 shown in FIG. 2 may be defined by the following equation:

$$Z_{aux} = \begin{cases} 0, & (0 \le r < r_1) \\ \dfrac{\Delta}{(r_2 - r_1)}(r - r_1), & (r_1 \le r < r_2) \\ \Delta, & (r_2 < r) \end{cases} \quad \text{Eq. (2a)}$$

wherein, r denotes a radial distance from the optical axis 105 of the optic 120, $r_1$ denotes a radial distance from the optical axis 105 to the first radial boundary 122;

$r_2$ denotes a radial distance from the optical axis 105 to the second radial boundary 124; and $\Delta$ denotes a step height of the phase shift structure 150 relative to the inner region 152;

and wherein, $\Delta$ is defined by the following relation:

$$\Delta = \dfrac{\alpha \lambda}{(n_2 - n_1)}, \quad \text{Eq. (2b)}$$

wherein, $n_1$ denotes an index of refraction of material forming the optic, $n_2$ denotes an index of refraction of a medium surrounding the optic, $\lambda$ denotes a design wavelength, and $\alpha$ denotes a non-integer fraction.

In an embodiment, the phase shift structure 150 defined by Eqs. (2a) and (2b) is characterized by a substantially linear phase shift across the transition region 154. More specifically, the phase shift structure 150 provides a phase shift that increases linearly from the inner boundary of the transition region 154 (corresponding to the first radial boundary 122) to the outer boundary of the transition region 154 (corresponding to the second radial boundary 124), with the optical path difference between the inner and the outer boundaries (or between the first and second radial boundaries 122, 124) corresponding to a non-integer fraction of the design wavelength.

In operation, the trapezoid phase shift structure 150 may produce continual focus shifts by means of a progressive wave front delay between the inner region 152 and the outer region 156, which results in a collective depth of focus extension. The phase shift structure may produce varying amounts of phase shift of light waves passing through the optic 120 (depending upon the region of the optic 120 the light waves pass through), and constructive interference between the light waves having varying amounts of phase shift may produce the extended depth of focus. As described below, an additional depth of focus extension may be achieved by adding the inner power zone 162 of the zonal structure 160 to the phase shift structure 150. In this case, the phase shift structure 150 may help to mitigate the undesired pupil-dependent focal shift that may result from the enhanced depth-of-focus extension caused by the inner power zone 162. Additionally, without the trapezoidal phase shift structure 150, the optic 120 would essentially function as a bifocal design.

In one embodiment, the radial distance, $r_1$, of the inner region 152 of the phase shift structure 150 (from the optical axis 105 to the first radial boundary 122) may comprise a value ranging from about 0.45 mm to 0.75 mm. The radial distance, $r_2$, from the optical axis 105 to the second radial boundary 124 may comprise a value ranging from about 0.75 mm to 1.05 mm Additionally, the step height, $\Delta$, of the phrase shift structure 150 may be approximately −2.1 μm.

With continued reference to FIG. 1A in conjunction with FIG. 2, the zonal structure 160 may include an inner power zone 162 and an outer transition zone 164. Inner power zone 162 may have a first curvature and may extend radially from the optical axis 105 to the second radial boundary 124 and, as shown in FIG. 2, may overlap with the inner and transition regions 152, 154 of the phase shift structure 150. The inner power zone 162 may comprise a refractive surface and may be disposed to enhance depth of focus for improved intermediate vision performance. Specifically, while the trapezoid phase shift structure 150 may itself have the capability to improve depth of focus and visual acuity for intermediate vision, the inner power zone 162, having an additional higher refractive power than the base structure 170, may yield an add power effect that, when combined with the phase shift structure 150, may further increase depth of focus and improve intermediate vision. Moreover, the combination of the trapezoid phase shift structure 150 and the inner power zone 162 may allow the optic to flexibly perform intermediate vision control in terms of both focal distance and power. In an embodiment, the inner power zone 162 is positioned in the innermost region of the optic 120. This positioning is particularly important to extend depth of focus up and improve visual acuity. In an embodiment, the range of add power in the inner power zone 162 may be from 0.7 D to 2.4 D. In an embodiment, the inner power zone 162 may extend depth of focus up to 2.38 D and improve visual acuity by 0.2 for pupil diameters of 2 mm to 6 mm.

In an embodiment, the inner power zone 162 shown in FIG. 2 may be defined by the following equation:

$$Z_{zone1} = \frac{c_1 r^2}{1 + \sqrt{1 - (1 + k_1)c_1^2 r^2}} + A_4' r^4 + A_6' r^6 (0 \le r < r_2) \quad \text{Eq. (3)}$$

wherein,
r denotes a radial distance from the optical axis 105 of the optic 120,
$c_1$ denotes a base curvature of the inner power zone 162,
$k_1$ denotes a conic constant,
$r_2$ denotes the radial distance from the optical axis 105 to the second radial boundary 124,
$A_4'$ is a fourth order aspheric coefficient, and
$A_6'$ is a sixth order aspheric coefficient.

In an embodiment, $r_2$ may comprise a value ranging from about 0.45 mm to 0.80 mm. In an embodiment, the value of $r_2$ in Eq. (3) for the inner power zone 162 may be substantially equivalent to the value of $r_2$ in Eq. (2a) for the trapezoid phase shift structure 150. In yet another embodiment, there may be some degree of variance between the value of $r_2$ in Eq. (3) for the inner power zone 162 and the value of $r_2$ in Eq. (2a) for the trapezoid phase shift structure 150. Thus, in some embodiments, the position of the second radial boundary 124 may be understood as a reference point which may vary or differ with respect to the independent structures, such as the phase shift structure 150 and the zonal structure 160, of the optic 120. The base curvature, $c_1$, of the inner power zone 162 may comprise a value ranging from about 19.0 to 20.2 $mm^{-1}$ for a mid-power diopter value of, e.g., 21D. The conic constant, $k_1$, may range in value from about −100 to −30. The fourth order aspheric coefficient, $A_4'$, may comprise a value ranging from about −6.5×10⁻⁴ to −1.0×10⁻⁴ $mm^{-3}$ The sixth order aspheric coefficient, $A_6'$, may comprise a value ranging from about −1.0×10⁻⁵ to 3.0×10⁻⁵ $mm^{-5}$ In an embodiment, the fourth and sixth order aspheric coefficients may be selected to optimize spherical aberration of the optic 120.

The zonal structure 160 may further include an outer transition zone 164 having a second curvature. As shown in the cross-sectional view of FIG. 2, the outer transition zone 164 may functionally extend radially from the second boundary 124 to the third boundary 126, wherein the third boundary 126 is disposed at a radial distance further from the optical axis 105 than the second boundary 124. While FIG. 2 depicts the functional boundaries of the outer transition zone 164 as extending radially from the second radial boundary 124 to the third radial boundary 126, it is to be understood that the structure forming the outer transition zone 164 technically extends radially from the optical axis 105 to the third radial boundary 126. However, the innermost region 164a of the outer transition zone 164, from the optical axis 105 to the second radial boundary 124 (depicted by the dotted lines), does not functionally contribute to the multi-layered surface profile of the anterior surface 130 of the optic 120. In other words, only the outermost region 164b of the outer transition zone 164 functionally contributes to the resultant sag 180 of the multi-layered surface profile of the anterior surface 130. Outer transition zone 164 may comprise a refractive surface, and may serve to provide a smooth transition from the inner power zone 162 to the base structure 170.

In some embodiments, outer transition zone 164 may be excluded from the design of the optic 120. In such embodiments, it is to be understood the remaining structures (e.g., phase shift structure 150, inner power zone 162, and/or base structure 170) may be modified to provide appropriate transition from the inner power zone 162 to the base structure 170. For example, the base structure 170 (described below) may be modified to functionally begin at the second radial boundary 124 (instead of the third radial boundary 126) and may extend radially to the outermost edge 128 of the optic. By way of further example, the superposition of the outer portion 162b of the inner power zone 162 of the zonal structure 160 and the transition zone 154 of the phase shift structure 150 may provide transition from the inner power zone 162 to the base structure 170. It is to be understood that these and other modifications to the optic are contemplated as within the scope of the present disclosure.

The outer transition zone 164 shown in FIG. 2 may be defined by the following equation:

$$Z_{zone2} = \frac{c_2 r^2}{1 + \sqrt{1 - (1+k_2)c_2^2 r^2}} + A_4'' r^4 + A_6'' r^6 (r_2 \leq r < r_3) \quad \text{Eq. (4)}$$

wherein,
r denotes a radial distance from the optical axis 105 of the optic 120,
$c_2$ denotes a base curvature of the outer transition zone 164,
$k_2$ denotes a conic constant,
$r_2$ denotes the radial distance from the optical axis 105 to the second radial boundary 124,
$r_3$ denotes the radial distance from the optical axis 105 to the third radial boundary 126,
$A_4''$ is a fourth order aspheric coefficient, and
$A_6''$ is a sixth order aspheric coefficient.

In an embodiment, the radial distance, $r_2$, from the optical axis 105 to the second radial boundary 124 may comprise a value ranging from about 0.45 mm to 0.80 mm. In an embodiment, the value of $r_2$ in Eq. (4) for the outer transition zone 162 may be substantially equivalent to the value of $r_2$ in Eq. (2a) for the trapezoid phase shift structure 150. In yet another embodiment, there may be some degree of variance between the value of $r_2$ in Eq. (4) for the outer transition zone 162 and the value of $r_2$ in Eq. (2a) for the trapezoid phase shift structure 150. The radial distance, $r_3$, from the optical axis 105 to the third radial boundary 126 may comprise a value ranging from about 0.60 mm to 1.2 mm. The base curvature, $c_2$, of the outer transition zone 164 may comprise a value ranging from about 20.0 to 20.5 mm$^{-1}$ The conic constant, $k_2$, may range in value from about $-100$ to $-30$. The fourth order aspheric coefficient, $A_4''$, may comprise a value ranging from $-6.5 \times 10^{-4}$ to $-1.0 \times 10^{-4}$ mm$^{-3}$ The sixth order aspheric coefficient, $A_6''$, may comprise a value ranging from about $-1.0 \times 10^{-5}$ to $3.0 \times 10^{-5}$ mm$^{-5}$.

With continued reference to FIG. 1A in conjunction with FIG. 2, the base structure 170 may comprise a third profile or structure of the multi-layered surface profile of the anterior surface 130 of the optic 120. In some embodiments, the base structure 170 may be in the form of a base curvature. As shown in the cross-sectional view of FIG. 2, the base structure 170 may functionally extend radially from the third radial boundary 126 to the outermost edge 128 of the optic. While FIG. 2 depicts the functional boundaries of the base curvature or base structure 170 (i.e., extending radially from the third radial boundary 126 to the outermost edge 128 of the optic), it is to be understood that the base structure 170 technically extends radially from the optical axis 105 to the outermost edge 128 of the optic 120. However, the innermost region 170a of the base structure 170 (depicted by the dotted lines, from the optical axis 105 to the third radial boundary 126) does not functionally contribute to the multi-layered surface profile of the anterior surface 130 of the optic 120. In other words, only the outermost region 170b of the base structure 170 functionally contributes to the resultant sag 180 of the multi-layered surface profile of the anterior surface 130.

In an embodiment, base structure 170 may comprise an aspheric surface profile having a base lens power, as that term is understood in the art. In an embodiment, the base structure may have an optical power ranging from $-15D$ to $+50D$.

The base structure 170 shown in FIG. 2 may be defined by the following equation:

$$Z_{base} = \frac{cr^2}{1 + \sqrt{1 - (1+k)c^2 r^2}} + A_4 r^4 + A_4 r^4 + A_6 r^6 \text{ where} \quad \text{Eq. (5)}$$

$r \geq r_3$ wherein,
r denotes a radial distance from the optical axis 105 of the optic 120,
c denotes a curvature of the base structure 170,
k denotes a conic constant,
$r_3$ denotes the radial distance from the optical axis to the third boundary 126,
$A_4$ is a fourth order aspheric coefficient, and
$A_6$ is a sixth order aspheric coefficient.

In an embodiment, the radial distance, $r_3$, from the optical axis 105 to the third radial boundary 126 may comprise a value ranging from about 0.60 mm to 1.2 mm. The base curvature, c, of the base structure 170 may comprise a value ranging from about 0.0152 mm$^{-1}$ to about 0.0659 mm$^{-1}$ The conic constant, k, may comprise a value ranging from about $-1162$ to about $-19$. The fourth order aspheric coefficient, $A_4$, may comprise a value ranging from about 0.0 mm$^{-3}$ to about $-5.3 \times 10^{-3}$ mm$^{-3}$ The sixth order aspheric coefficient, $A_6$, may comprise a value ranging from about 0.0 mm$^{-3}$ to about $1.53 \times 10^{-4}$ mm$^{-5}$.

With further reference to FIG. 2, and as described above, the superposition of structures 150, 160, 170 may result in the composite multi-layered surface profile (labeled "resultant sag" 180 in FIG. 2). The resultant sag 180 may further correspond to first, second, third, and fourth regions 182, 184, 186, 188 defined by radial boundaries 122, 124, 126, 128, respectively. Each of the first, second, third, and fourth regions 182, 184, 186, 188 of resultant sag 180 may result from the composite contributions of one or more of the structures 150, 160, 170 described above.

For example, first region 182 of the resultant sag 180 may be defined as a region extending radially from the optical axis 105 to the first radial boundary 122. In an embodiment, the first region 182 may be formed by the superposition of the inner region 152 of phase shift structure 150 and an inner portion 162a of the inner power zone 162 of the zonal structure 160. In an embodiment, first region 182 may not include contributions from the outer transition zone 164 of the zonal structure 160 (e.g., the innermost region 164a of the outer transition zone 164) or the base structure 170 (e.g., the innermost region 170a of the base structure) because, as discussed above, the innermost region 164a of the outer transition zone 164 and the innermost region 170a of the base structure do not functionally contribute to the resultant sag 180 of the first region 182. In yet another embodiment, first region 182 of the resultant sag 180 may be defined by only the inner power zone 162, and more specifically, the inner portion 162a of the inner power zone 162. In other words, the inner region 152 of the phase shift structure may not functionally contribute to the resultant sag. First region 182 may comprise a first composite aspheric profile.

Second region 184 of the resultant sag 180 may be defined as a region extending radially from the first radial boundary 122 to the second radial boundary 124. In an embodiment, the second region 184 may be formed by the superposition of the transition region 154 of phase shift structure 150 and an outer portion 162b of the inner power zone 162 of the zonal structure 160. In an embodiment, second region 184 may not include contributions from the outer transition zone 164 of the zonal structure 160 (e.g., the innermost region 164a of the outer transition zone 164) or the base structure 170 (e.g., the innermost region 170a of the base structure) because the innermost region 164a of the outer transition zone 164 and the innermost region 170a of the base structure 170 do not functionally contribute to the resultant sag 180 of the second region 184. The transition region 154 (having the single-step phase shift), when combined with the outer portion 162b of the inner power zone 162, may allow resultant second region 184 to serve as a transition from the first region 182 to the third region 186. The second region 184 may comprise a second composite aspheric profile.

With continued reference to FIG. 2, third region 186 of the resultant sag 180 may be defined as a region extending radially from the second radial boundary 124 to the third radial boundary 126. In an embodiment, the third region 186 may be formed by the superposition of the outermost region 164b of the outer transition zone 164 of the zonal structure 160 and the outer region 156 of the phase shift structure 150. The third region 186, which is a combination of the outermost region 164b of the outer transition zone 164 and the outer region 156, may serve as a transition from the second region 184 to the fourth region 188. In an embodiment, third region 186 may not include contributions from the base structure 170 (e.g., the innermost region 170a of the base structure) because the innermost region 170a of the base structure does not functionally contribute to the resultant sag 180 of the third region 186. In yet another embodiment, third region 186 may only be defined by the outer transition zone 164 of the zonal structure 160, and more specifically, the outermost region 164b of the outer transition zone 164. In other words, the outer region 156 of the phase shift structure may not functionally contribute to the resultant sag. The third region 186 may comprise a third composite aspheric profile.

Fourth region 188 of the resultant sag 180 may be defined as region extending radially from the third radial boundary 126 to the outermost edge 128 of the optic. In an embodiment, the fourth region 188 may be formed by the superposition of the outer region 156 of the phase shift structure 150 and the base structure 170. In yet another embodiment, fourth region 188 may be defined by only the base structure 170. In other words, the outer region 156 of the phase shift structure 150 may not functionally contribute to the resultant sag. The fourth region 188 may comprise a fourth composite aspheric profile.

In sum, the fundamental geometry encompassed by the example optic of FIGS. 1A and 2 and defined by Equations (1) to (5) is the combination of a trapezoid phase shift structure and a zonal refractive surface having an add power effect, which together may improve intermediate vision performance and extend depth of focus, while maintaining distance vision. It is to be understood that various modifications, enhancements, and adjustments may be made to the optic 120 described herein without departing from the spirit and the scope of the disclosure.

Figure 3A:
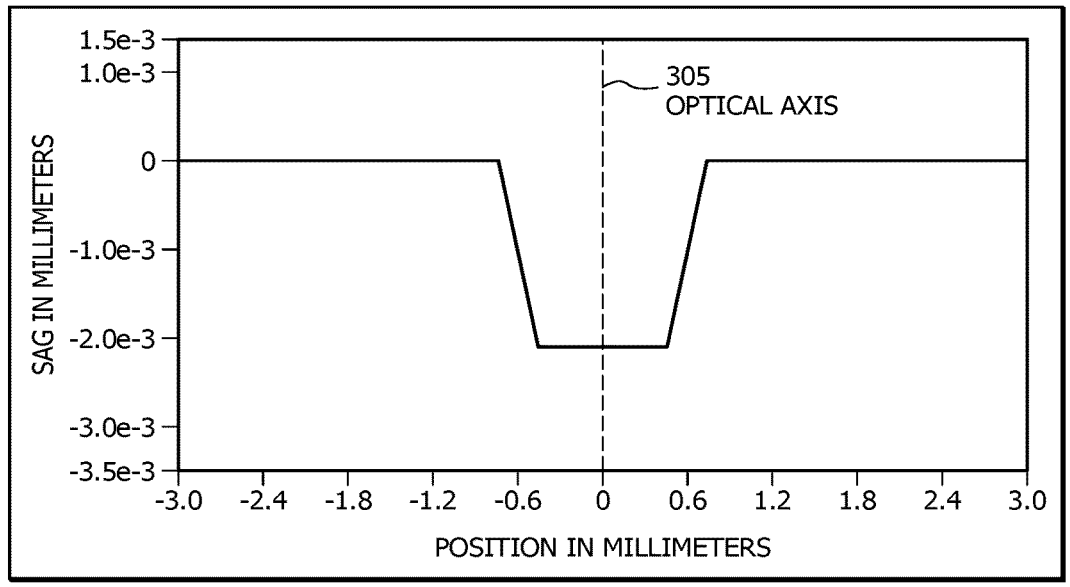
FIG. 3A illustrates a plot of the surface sag versus radial distance from the optical axis for a phase shift structure of an example optic, in accordance with the present disclosure.
Figure 3B:
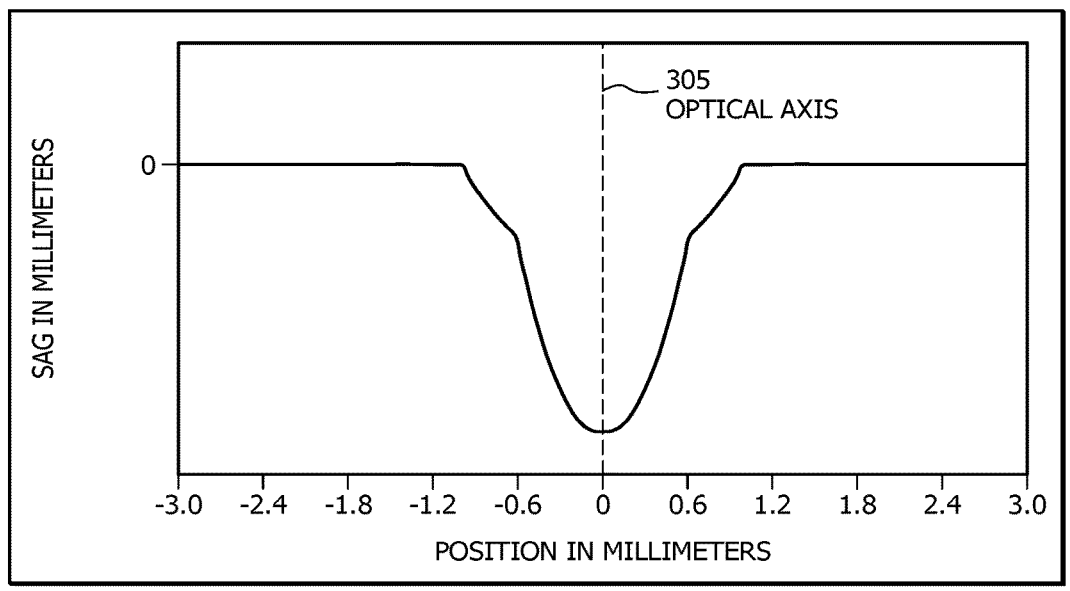
FIG. 3B illustrates a plot of the surface sag versus radial distance from the optical axis for a zonal structure of an example optic, in accordance with the present disclosure.
Figure 3C:
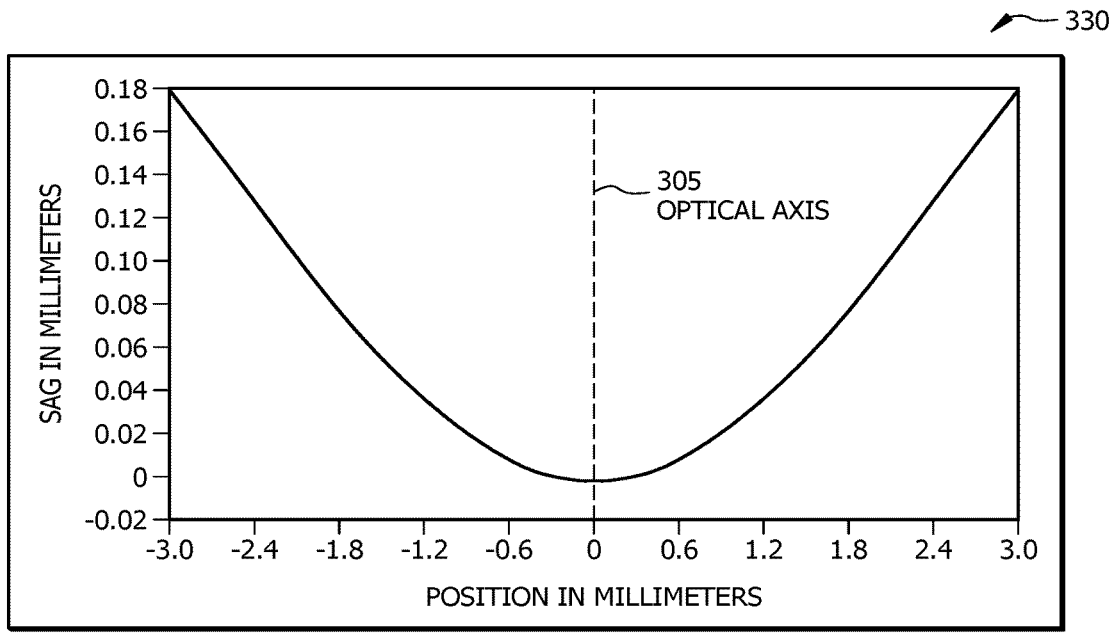
FIG. 3C illustrates a plot of the composite surface sag versus radial distance from the optical axis for an example optic, in accordance with the present disclosure.

Reference is now made to FIGS. 3A-3C that show the surface profile of the anterior surface 130 of the optic 120 shown in FIGS. 1A and 2 and defined by Eqs. (1) to (5), graphically represented as plots 310, 320, and 330 of sag versus radial distance from the optical axis 105 of the optic 120. Specifically, FIG. 3A depicts a sag plot 310 for the trapezoid phrase shift structure (element 150 of FIG. 2) of the optic 120. FIG. 3B depicts a unitless sag plot 320 for the zonal structure (element 160 of FIG. 2) of the optic 120. FIG. 3C depicts a sag plot 330 of the composite multi-layered surface profile of the anterior surface 130 of the optic 120. In all three plots of FIGS. 3A-3C, the radius is zero at optical axis 305. As shown in the FIG. 3C, the sag curve is substantially parabolic, consistent with an aspheric lens surface. It is to be understood that FIGS. 3A-3C are shown for illustration purposes only, i.e., to show the shapes of the curves, and therefore may not be to scale and may not show the positions of the curves as a function of particular data points and/or units of measurement.

Figure 4A:
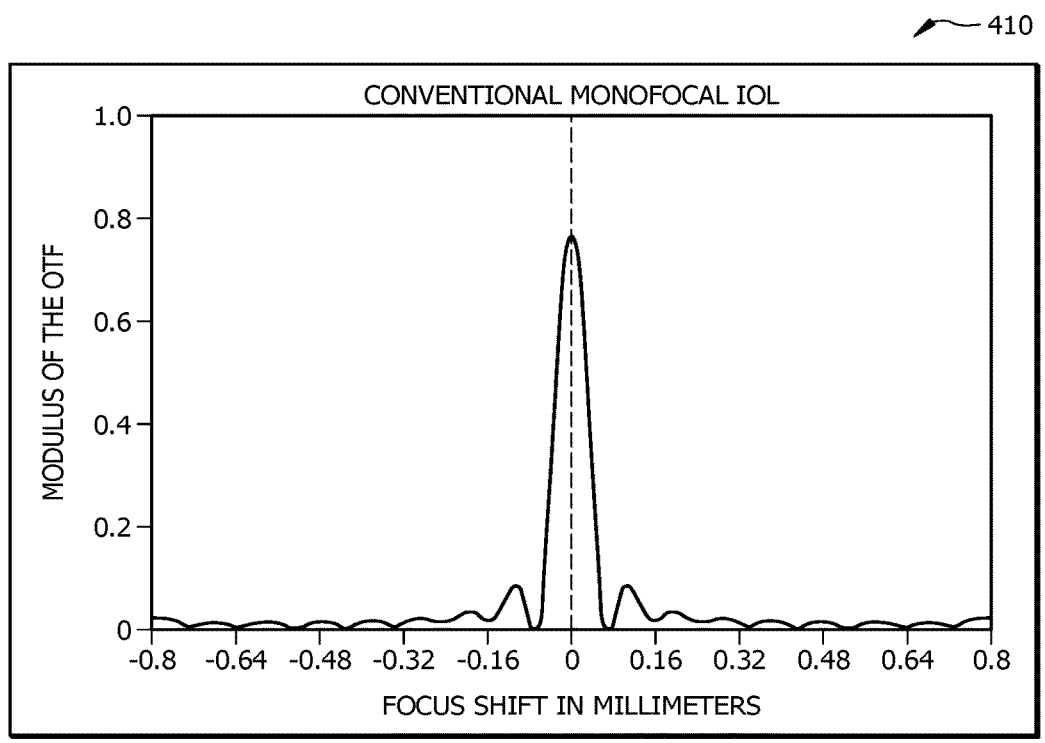
FIG. 4A illustrates a through-focus modulation transfer function (MTF) plot for a conventional monofocal IOL, in accordance with the present disclosure.
Figure 4B:
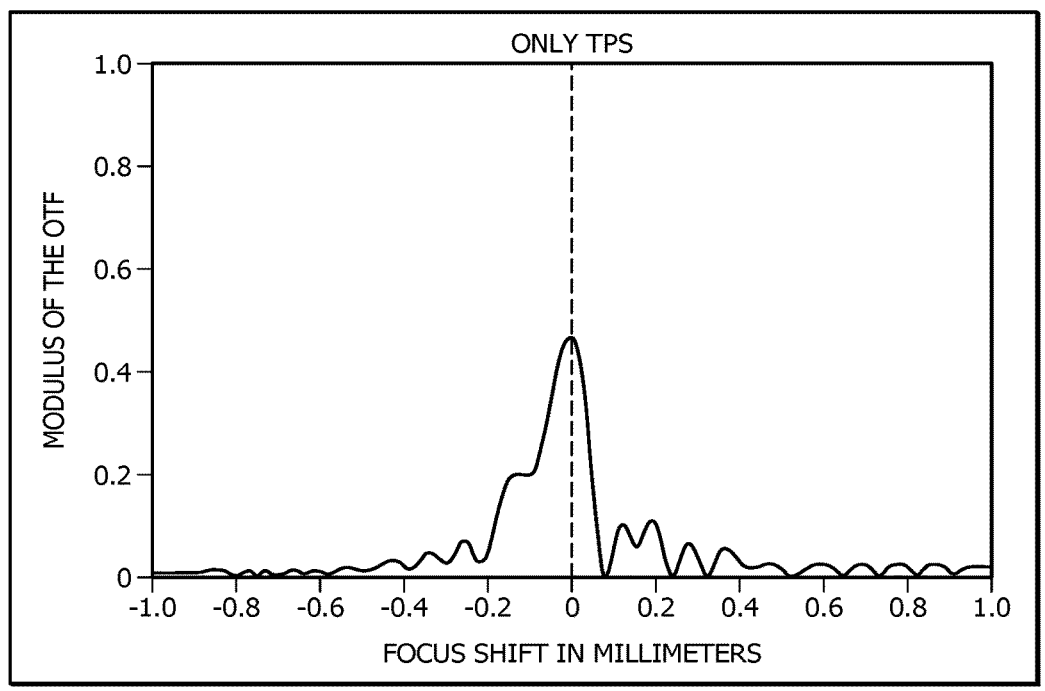
FIG. 4B illustrates a through-focus MTF plot for an optic having only a phase shift structure, in accordance with the present disclosure.
Figure 4C:
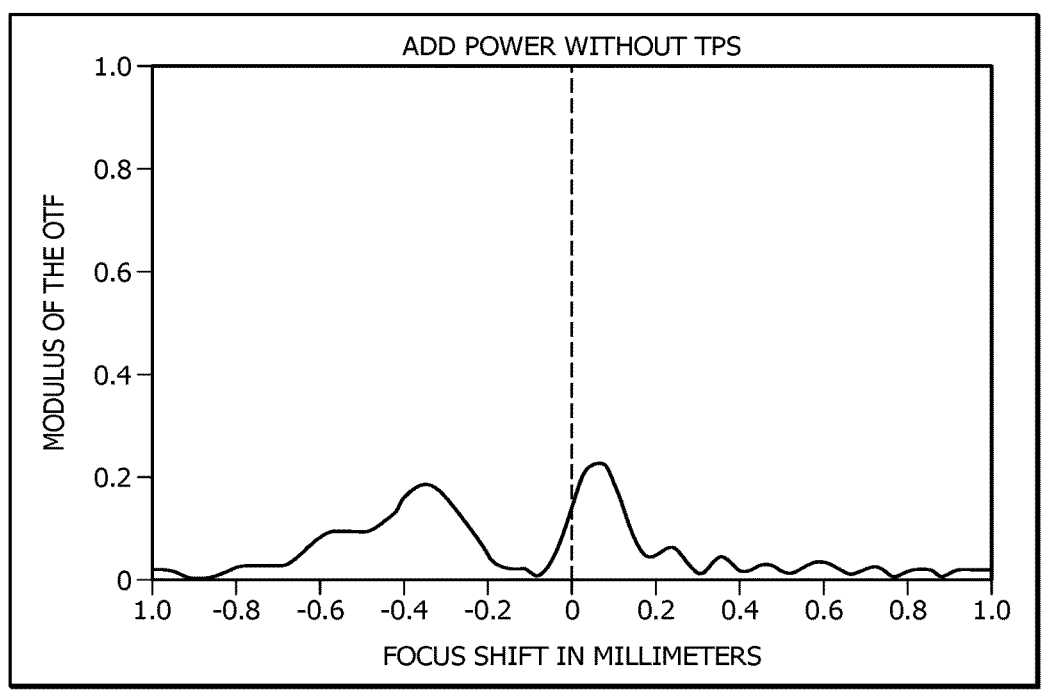
FIG. 4C illustrates a through-focus MTF plot for an optic having only a zonal power structure, in accordance with the present disclosure.
Figure 4D:
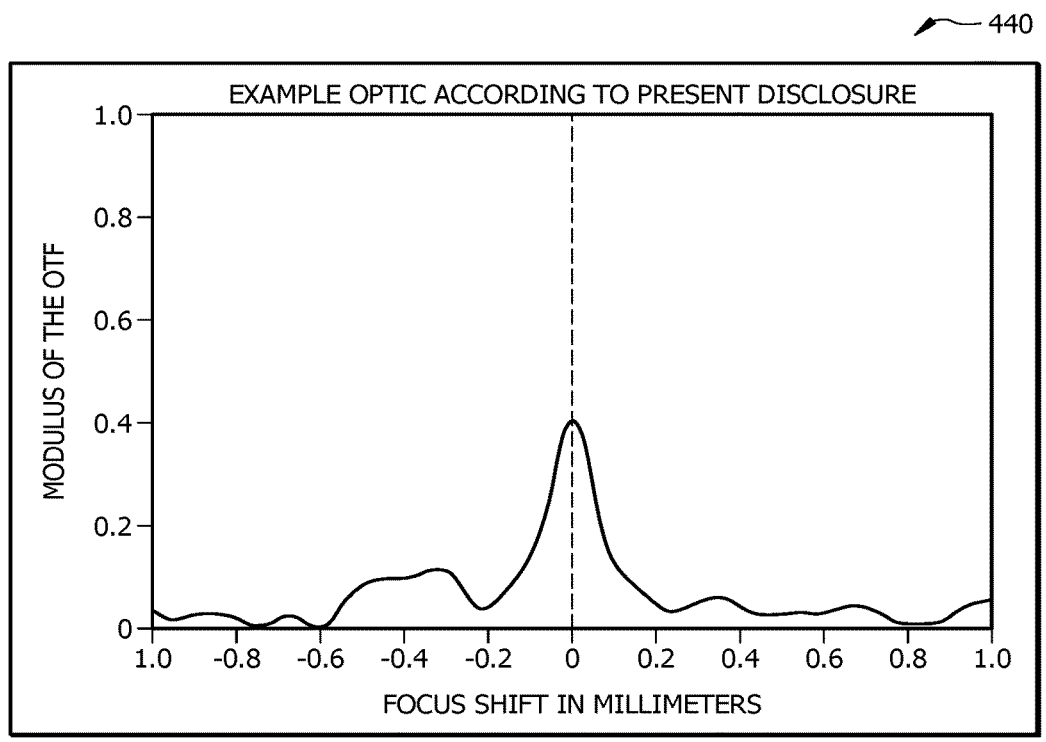
FIG. 4D illustrates a through-focus MTF plot for an example optic, in accordance with the present disclosure.

Reference is now made to FIGS. 4A-4D that show the through-focus modulation transfer function (MTF) plots 410, 420, 430, 440 for four optics. FIG. 4A shows an MTF plot 410 for an optic of a monofocal IOL. FIG. 4B shows an MTF plot 420 for an optic having a trapezoid phase shift (TPS) structure (with no zonal add power structure). FIG. 4C shows an MTF plot 430 for an optic having a zonal add power structure (with no phase shift structure). FIG. 4D shows an MTF plot 440 of an example optic 120 based on the design shown in FIGS. 1A and 2 and defined by Eqs. (1) to (5). These plots 410, 420, 430, 440 may be comparatively analyzed to further understand the improvements offered by the example optic design (depicted in plot 440) of the present disclosure. For example, as shown in FIG. 4A, an optic of a monofocal IOL lacks extended depth of focus. Next, as shown in FIG. 4B, the optic having a trapezoid phase shift structure (with no zonal add power structure) has limited range of depth of focus and poor MTF at the defocus above the 0.5 D (myopic side) range. Third, as shown in FIG. 4C, the optic having a zonal add power structure (with no phase shift structure) demonstrates bifocality, as evidenced by two distinct peaks at positive and negative focal shifts. This strong bifocality may cause undesired pupil-dependent focal shift and/or halos. Finally, as shown in FIG. 4D, the example optic based on the design shown in FIGS. 1A and 2 and defined by Eqs. (1) to (5) of the present disclosure provides extended intermediate vision without sacrificing distance vision and with no more visual disturbances than that of a monofocal IOL. As further shown in FIG. 4D, the example optic further provides enhanced depth of focus extension and MTF performance in the intermediate vision, e.g., particularly at 1.0 D to approximately 1.5 D.

Figure 5:
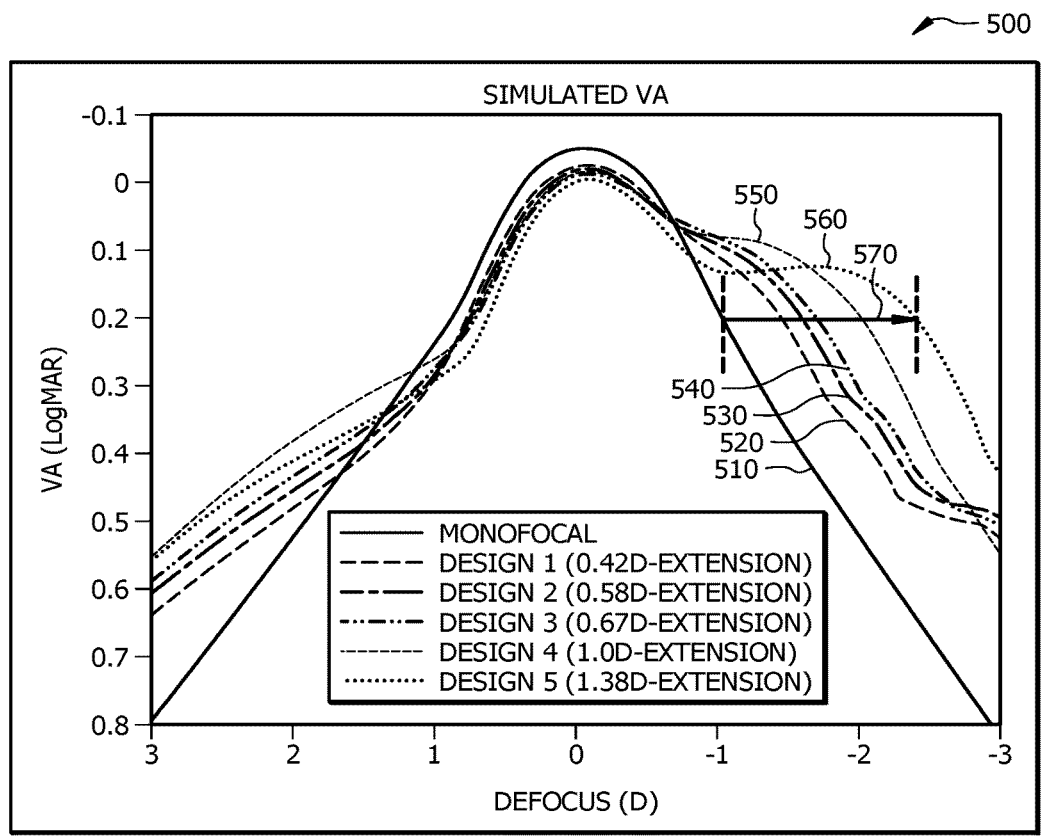
FIG. 5 illustrates a graph of visual acuity (VA) versus defocus and depicts depth of focus extensions for example optics, in accordance with the present disclosure.

Reference is now made to FIG. 5 that shows simulated monocular visual acuity (VA) plots 500 for example optics based on the design shown in FIGS. 1A and 2 and defined by Eqs. (1) to (5). Visual acuity (VA) is the primary measure of visual function in both clinical practice and research. VA may be modeled using the intersection of the eye's modulation transfer function (MTF) with a retinal threshold function. In FIG. 5, the solid black curve 510 represents a monofocal IOL, and the plurality of dotted curves 520, 530, 540, 550, 560 represent example optics according the present disclosure. Each of the example optics is associated with a different add-power extension, as set forth in the graph. As shown in FIG. 5, each of the curves of the example optics 520, 530, 540, 550, 560 shows a depth of focus extension over the monofocal IOL 510. The depth of focus extensions range from 0.42 D in example optic 520 to a maximum depth of focus extension reaching 1.38 D (shown as 570) in example optic 560. While there is a small tradeoff in visual acuity as the depth of focus is extended, it is to be understood that an optimal design may attempt to balance these considerations.

In use, the intraocular lenses described herein are adapted to be inserted in the human eye using conventional surgical techniques modified in accordance with the present teachings. Typically, the natural crystalline lens is first removed and the IOL can be folded into a compact size for insertion through an incision or opening in the capsular bag. Following insertion, the IOL may be manipulated to assume its proper position in the capsular bag.

A variety of techniques and materials may be employed to fabricate the lenses described in this disclosure. For example, the optic 120 of FIGS. 1A and 1B may be formed of a variety of biocompatible polymeric materials. Some suitable biocompatible materials include, without limitation, soft acrylic polymers, hydrogel, polymethymethacrylate, polysulfone, polystyrene, cellulose, acetate butyrate, or other biocompatible materials. By way of example, in an embodiment, the optic 120 may be formed of a soft acrylic polymer (cross-linked copolymer of 2-phenylethyl acrylate and 2-phenyl-ethyl methacrylate) commonly known as Acrysof®. The haptics 110 of the lenses may be formed of suitable biocompatible materials, such as those discussed above. While in some cases the optic 120 and the haptics 110 of an IOL can be fabricated as an integral unit, in other cases they can be formed separately and joined together using techniques known in the art.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

It will be appreciated that various of the above-disclosed and other features and functions, or alternatives thereof, may be desirably combined into many other different systems or applications. It will also be appreciated that various presently unforeseen or unanticipated alternative, modifications, variations, or improvements therein may be subsequently made by those skilled in the art which alternatives, variations, and improvements are also intended to be encompassed by the following claims. Those having ordinary skill in the art will appreciate that various changes can be made to the above embodiments without departing from the scope of the invention.

The invention claimed is:

1. An ophthalmic lens, comprising:
an optic having an anterior surface and a posterior surface disposed about an optical axis, at least one of the anterior and posterior surfaces having a composite multi-layered surface profile corresponding to a superposition of at least three profiles comprising a phase shift structure, a zonal structure, and a base structure:
the zonal structure having an inner power zone having a first curvature and an outer transition zone having a second curvature; and
the base structure having a base curvature extending radially from the optical axis to an outermost edge of the optic.

2. The ophthalmic lens of claim 1, wherein the phase shift structure is characterized by an inner region, an outer region, and a transition region, wherein:
the inner region extends radially from the optical axis to a first boundary;
the transition region is disposed between the inner region and the outer region and extends radially from the first boundary to a second boundary, the second boundary disposed at a radial distance further from the optical axis than the first boundary; and
the outer region extends radially from the second boundary towards the outermost edge of the optic.

3. The ophthalmic lens of claim 2, wherein the transition region is adapted such that a phase of radiation incident thereon varies linearly over at least a portion of the radial extent between the first boundary and the second boundary so as to generate a phase shift between the first and second boundaries.

4. The ophthalmic lens of claim 2, wherein the inner power zone extends radially from the optical axis to the second boundary, and the outer transition zone extends radially from the optical axis to a third boundary, the third boundary disposed at a radial distance further from the optical axis than the second boundary.

5. The ophthalmic lens of claim 4, wherein:
a first region of the optic comprises a first composite aspheric profile, the first region defined from the optical axis and extending radially to the first boundary;
a second region of the optic comprises a second composite aspheric profile, the second region defined from the first boundary and extending radially to the second boundary;
a third region of the optic comprises a third composite aspheric profile, the third region defined from the second boundary and extending radially to the third boundary; and
a fourth region of the optic comprises a fourth composite aspheric profile, the fourth region defined from the third boundary to the outermost edge of the optic.

6. The ophthalmic lens of claim 2, wherein the composite multi-layered surface profile of the at least one of the anterior and posterior surfaces is described by the following equation:

$$Z_{total} = Z_{aux} + Z_{zone1} + Z_{zone2} + Z_{base}.$$

7. The ophthalmic lens of claim 6, wherein Zaux corresponds to the phase shift structure and is described by the following equation:

$$Z_{aux} = \begin{cases} 0, & (0 \le r < r_1) \\ \frac{\Delta}{(r_2 - r_1)}(r - r_1), & (r_1 \le r < r_2) \\ \Delta, & (r_2 < r) \end{cases}$$

wherein,
r denotes a radial distance from the optical axis of the optic,
r1 denotes a radial distance from the optical axis to the first boundary;
r2 denotes a radial distance from the optical axis to the second boundary;
and wherein,
$\Delta$ is defined by the following relation:

$$\Delta = \frac{\alpha\lambda}{(n_2 - n_1)},$$

wherein,
- n1 denotes an index of refraction of material forming the optic,
- n2 denotes an index of refraction of a medium surrounding the optic,
- λ denotes a design wavelength, and
- α denotes a non-integer fraction.

8. The ophthalmic lens of claim 7, wherein r1 comprises a value ranging from 0.45 mm to 0.75 mm.

9. The ophthalmic lens of claim 7, wherein r2 comprises a value ranging from 0.75 mm to 1.05 mm.

10. The ophthalmic lens of claim 6, wherein Zzone1 corresponds to the inner power zone and is described by the following equation:

$$Z_{zone1} = \frac{c_1 r^2}{1 + \sqrt{1 - (1 + k_1)c_1^2 r^2}} + A_4' r^4 + A_6' r^6 \; (0 \leq r < r_2)$$

wherein,
- r denotes a radial distance from the optical axis of the optic,
- c1 denotes the first curvature of the inner power zone,
- k1 denotes a conic constant,
- r2 denotes a radial distance from the optical axis to the second boundary,
- A4' is a fourth order aspheric coefficient, and
- A6' is a sixth order aspheric coefficient.

11. The ophthalmic lens of claim 10, wherein r2 comprises a value ranging from 0.45 mm to 0.80 mm.

12. The ophthalmic lens of claim 6, wherein Zzone2 corresponds to the outer transition zone and is described by the following equation:

$$Z_{zone2} = \frac{c_2 r^2}{1 + \sqrt{1 - (1 + k_2)c_2^2 r^2}} + A_4'' r^4 + A_6'' r^6 \; (r_2 \leq r < r_3)$$

wherein,
- r denotes a radial distance from the optical axis of the optic,
- c2 denotes the second curvature of the outer transition zone,
- k2 denotes a conic constant,
- r2 denotes a radial distance from the optical axis to the second boundary,
- r3 denotes a radial distance from the optical axis to a third boundary,
- A4" is a fourth order aspheric coefficient, and
- A6" is a sixth order aspheric coefficient.

13. The ophthalmic lens of claim 12, wherein r2 comprises a value ranging from 0.45 mm to 0.80 mm.

14. The ophthalmic lens of claim 12, wherein r3 comprises a value ranging from 0.60 mm to 1.20 mm.

15. The ophthalmic lens of claim 6, wherein Zbase corresponds to the base curvature and is described by the following equation:

$$Z_{base} = \frac{c r^2}{1 + \sqrt{1 - (1 + k)c^2 r^2}} + A_4 r^4 + A_6 r^6 \; \text{where } r \geq r_3$$

wherein,
- r denotes a radial distance from the optical axis of the optic,
- c denotes a value of the base curvature,
- k denotes a conic constant,
- r3 denotes a radial distance from the optical axis to a third boundary,
- A4 is a fourth order aspheric coefficient, and
- A6 is a sixth order aspheric coefficient.

16. The ophthalmic lens of claim 15, wherein r3 comprises a value ranging from 0.60 mm to 1.20 mm.

17. The ophthalmic lens of claim 1, wherein the inner power zone is disposed to enhance depth of focus for intermediate vision performance.

18. The ophthalmic lens of claim 17, wherein the phase shift structure is disposed to mitigate pupil-dependent focal shift effect caused by the enhanced depth of focus by the inner power zone.

19. A method of treating a vision disorder, comprising:
inserting an ophthalmic lens within a capsular bag of a patient's eye, the ophthalmic lens comprising:
an optic having an anterior surface and a posterior surface disposed about an optical axis,
at least one of the anterior and posterior surfaces having a surface profile corresponding to:
a phase shift structure characterized by an inner region, an outer region, and a transition region, wherein,
the inner region extends radially from the optical axis to a first boundary;
the transition region is disposed between the inner region and the outer region and extends radially from the first boundary to a second boundary, wherein the transition region is adapted such that a phase of radiation incident thereon varies linearly over at least a portion of the radial extent between the first boundary and the second boundary so as to generate a phase shift between the first and second boundaries, the second boundary disposed at a radial distance further from the optical axis than the first boundary; and
the outer region extends radially from the second boundary towards an outermost edge of the optic;
a zonal structure having an inner power zone having a first curvature and an outer transition zone having a second curvature, wherein the inner power zone extends radially from the optical axis to the second boundary and the outer transition zone extends radially to a third boundary, the third boundary disposed at a radial distance further from the optical axis than the second boundary; and
a base curvature extending radially from the third boundary to the outermost edge of the optic.

20. The method of claim 19, wherein:
a first region of the optic comprises a first composite aspheric profile, the first region defined from the optical axis and extending radially to the first boundary;
a second region of the optic comprises a second composite aspheric profile, the second region defined from the first boundary and extending radially to the second boundary;
a third region of the optic comprises a third composite aspheric profile, the third region defined from the second boundary and extending radially to the third boundary; and a fourth region of the optic comprises a fourth composite aspheric profile, the fourth region defined from the third boundary to the outermost edge of the optic.

* * * * *